(12) United States Patent
Magot et al.

(10) Patent No.: US 6,531,281 B1
(45) Date of Patent: Mar. 11, 2003

(54) METHOD OF DETECTING SULPHATE-REDUCING BACTERIA

(75) Inventors: Michel Magot, Saint-Orens de Gameville (FR); Gilles Ravot, Generac (FR)

(73) Assignee: Elf Exploration Production (FR)

( * ) Notice: Subject to any disclaimer, the term of this patent is extended or adjusted under 35 U.S.C. 154(b) by 0 days.

(21) Appl. No.: 09/535,012

(22) Filed: Mar. 24, 2000

(30) Foreign Application Priority Data

Mar. 24, 1999 (FR) .............................................. 99 03637

(51) Int. Cl.$^7$ ................................................. C12Q 1/68
(52) U.S. Cl. ........................ 435/6; 435/91.2; 536/23.1; 536/23.2; 536/24.3; 536/24.32; 536/24.33
(58) Field of Search .................. 435/6, 91.1; 536/23.1, 536/24.3, 24.32, 24.33, 23.2

(56) References Cited

U.S. PATENT DOCUMENTS

| | | | |
|---|---|---|---|
| 4,999,286 A | | 3/1991 | Gawel et al. ............... 435/7.32 |
| 5,369,011 A | | 11/1994 | Ebersole et al. ............ 435/7.32 |
| 5,595,874 A | * | 1/1997 | Hogan ........................... 435/6 |

FOREIGN PATENT DOCUMENTS

| EP | 0 502 271 | 9/1992 |
|---|---|---|
| GB | 2 189 317 | 10/1987 |

OTHER PUBLICATIONS

Friedrich et al. "Phylogenetic ANalyasis reveral multiple lateral transfers of adenosine–5' phosphosulfate reductase genes amon sulphate–reducing microorganisms" J. of Bacteriology, Jan. 2002, pp. 278–289, vol. 184, No. 1.*

Zinkevich et al. "Screening of sulfate–reducing bacteria in colonscopy samples from healthy and colitic human gut mucosa" FEMS Microbiology Ecology. Dec. 2000, pp. 147–155, vol. 34, No. 2.*

Deplancke et al. "molecular Ecological ANalysis of the succession and diversity of sulfate–reducing bacteria in the mouse gastrointestinal tract" Applied and Environmental Microbiology, VOl 66, No. 5, p. 2166–2174, May 2000.*

Speich et al. "Adenylylsulphate redductase from the sulphate reducing archaeon Archeaoglobus fulgidus" Microbiology, vol. 140, pg. 1273–1284, 1994.*

Genbank Accession No. A11737, Jul. 1994.*
Genbank Accession No. Y10088, Jun. 1997.*
Genbank Accession No. U32736, May 1998.*
Genbank Accession No. AJ242804, Nov. 1999.*
Genbank Accession No. AC004259, Jun. 1998.*
Genbank Accession No. AC017491, Dec. 1999.*
Genbank Accession No. AF107047, Dec. 1998.*
Genbank Accession No. AF161269, Aug. 1999.*
Genbank Accession No. U86914, May 1997.*
Genbank Accession No. E02368, Sep. 1997.*
Genbank Accession No. X05003, Oct. 1996.*
Genbank Accession No. AF024439, Oct. 1997.*
Genbank Accession No. AA842758, Mar. 1998.*
Genbank Accession No. U82207, Dec. 1998.*
Genbank Accession No. G28859, Sep. 1998.*
Genbank Accession No. D10483, Jun. 1997.*
Genbank Accession No. AL096825, Jul. 1999.*
Genbank Accession No. Z84817, Oct. 1997.*
Genbank Accession No. AF041202, Jan. 1998.*
Genbank Accession No. AC008353, Dec. 1999.*
Genbank Accession No. AJ006231, Sep. 1998.*

* cited by examiner

Primary Examiner—W. Gary Jones
Assistant Examiner—Jeanine Goldberg
(74) Attorney, Agent, or Firm—Blank Rome LLP (57) ABSTRACT

The present invention relates to a method for the detection of sulphate-reducing bacteria in a sample which is likely to contain them, the said method comprising the extraction of the DNA or of the RNA from the said sample and the detection of at least one fragment of the APS reductase gene or at least one fragment of the mRNA transcribed from the APS reductase gene, an indicator of the presence of sulphate-reducing bacteria in the said sample.

3 Claims, 3 Drawing Sheets apr A : subunit α
apr B : subunit β
pBS : potential fixation site of APS

FIG. 3 apr A : subunit α
pBS : potential fixation site of APS

SEQUENCE LISTING

```
<160> NUMBER OF SEQ ID NOS: 25

<210> SEQ ID NO 1
<211> LENGTH: 18
<212> TYPE: DNA
<213> ORGANISM: Desulfovibrio vulgaris
<220> FEATURE:
<223> OTHER INFORMATION: APS01 primer

<400> SEQUENCE: 1
cggcgccgtt gcccaggg                                                 18

<210> SEQ ID NO 2
<211> LENGTH: 18
<212> TYPE: DNA
<213> ORGANISM: Desulfovibrio vulgaris
<220> FEATURE:
<223> OTHER INFORMATION: APS02 primer

<400> SEQUENCE: 2
tctgttcgaa gagtgggg                                                 18

<210> SEQ ID NO 3
<211> LENGTH: 18
<212> TYPE: DNA
<213> ORGANISM: Desulfovibrio vulgaris
<220> FEATURE:
<223> OTHER INFORMATION: APS03 primer

<400> SEQUENCE: 3
ttcaaggacg gttacggc                                                 18

<210> SEQ ID NO 4
<211> LENGTH: 18
<212> TYPE: DNA
<213> ORGANISM: Desulfovibrio vulgaris
```

```
<220> FEATURE:
<223> OTHER INFORMATION: APS04 primer

<400> SEQUENCE: 4
cttcaagcac ggttacgg                                              18

<210> SEQ ID NO 5
<211> LENGTH: 18
<212> TYPE: DNA
<213> ORGANISM: Desulfovibrio vulgaris
<220> FEATURE:
<223> OTHER INFORMATION: APS05 primer
<223> OTHER INFORMATION: where N is A, C, G or T; H is A, C or T; Y is
      C or T

<400> SEQUENCE: 5
tcngccatha ayacntac                                              18

<210> SEQ ID NO 6
<211> LENGTH: 18
<212> TYPE: DNA
<213> ORGANISM: Desulfovibrio vulgaris
<220> FEATURE:
<223> OTHER INFORMATION: APS06 primer

<400> SEQUENCE: 6
gcagatcatg atcaacgg                                              18

<210> SEQ ID NO 7
<211> LENGTH: 18
<212> TYPE: DNA
<213> ORGANISM: Desulfovibrio vulgaris
<220> FEATURE:
<223> OTHER INFORMATION: APS11 primer

<400> SEQUENCE: 7
gggccgtaac cgtccttg                                              18

<210> SEQ ID NO 8
<211> LENGTH: 18
<212> TYPE: DNA
<213> ORGANISM: Desulfovibrio vulgaris
<220> FEATURE:
<223> OTHER INFORMATION: APS12 primer

<400> SEQUENCE: 8
tcacgaagca cttccact                                              18

<210> SEQ ID NO 9
<211> LENGTH: 18
<212> TYPE: DNA
<213> ORGANISM: Desulfovibrio vulgaris
<220> FEATURE:
<223> OTHER INFORMATION: APS13 primer

<400> SEQUENCE: 9
gcacatgtcg aggaagtc                                              18

<210> SEQ ID NO 10
<211> LENGTH: 18
<212> TYPE: DNA
<213> ORGANISM: Desulfovibrio vulgaris
<220> FEATURE:
<223> OTHER INFORMATION: APS14 primer

<400> SEQUENCE: 10
```

```
accggaggag aacttgtg                                                    18

<210> SEQ ID NO 11
<211> LENGTH: 17
<212> TYPE: DNA
<213> ORGANISM: Desulfovibrio vulgaris
<220> FEATURE:
<223> OTHER INFORMATION: asp01 primer

<400> SEQUENCE: 11
gatggaaaac cgcttcg                                                     17

<210> SEQ ID NO 12
<211> LENGTH: 17
<212> TYPE: DNA
<213> ORGANISM: Desulfovibrio vulgaris
<220> FEATURE:
<223> OTHER INFORMATION: asp02 primer

<400> SEQUENCE: 12
aagttctcct ccggttc                                                     17

<210> SEQ ID NO 13
<211> LENGTH: 17
<212> TYPE: DNA
<213> ORGANISM: Desulfovibrio vulgaris
<220> FEATURE:
<223> OTHER INFORMATION: asp03 primer

<400> SEQUENCE: 13
accatgatgg aaaaccg                                                     17

<210> SEQ ID NO 14
<211> LENGTH: 17
<212> TYPE: DNA
<213> ORGANISM: Desulfovibrio vulgaris
<220> FEATURE:
<223> OTHER INFORMATION: asp04 primer

<400> SEQUENCE: 14
tgaccatgat ggaaaac                                                17

<210> SEQ ID NO 15
<211> LENGTH: 17
<212> TYPE: DNA
<213> ORGANISM: Desulfovibrio vulgaris
<220> FEATURE:
<223> OTHER INFORMATION: asp11 primer

<400> SEQUENCE: 15
cgaagcatca tgtggtt                                                     17

<210> SEQ ID NO 16
<211> LENGTH: 17
<212> TYPE: DNA
<213> ORGANISM: Desulfovibrio vulgaris
<220> FEATURE:
<223> OTHER INFORMATION: asp12 primer

<400> SEQUENCE: 16
ccggaggaga acttgtg                                                     17

<210> SEQ ID NO 17
<211> LENGTH: 17
<212> TYPE: DNA
<213> ORGANISM: Desulfovibrio vulgaris
```

```
<220> FEATURE:
<223> OTHER INFORMATION: asp13 primer

<400> SEQUENCE: 17
aggcgcatca tgaagtt                                                    17

<210> SEQ ID NO 18
<211> LENGTH: 17
<212> TYPE: DNA
<213> ORGANISM: Desulfovibrio vulgaris
<220> FEATURE:
<223> OTHER INFORMATION: asp14 primer

<400> SEQUENCE: 18
atgtgctgca tgtgcag                                                    17

<210> SEQ ID NO 19
<211> LENGTH: 23
<212> TYPE: DNA
<213> ORGANISM: Desulfovibrio vulgaris
<220> FEATURE:
<223> OTHER INFORMATION: Snbsr1 oligonucleotide, where H is A , C or T;
      K is G or T; Y is C or T

<400> SEQUENCE: 19
gacggttacg ghcckgtygg ygc                                             23

<210> SEQ ID NO 20
<211> LENGTH: 32
<212> TYPE: DNA
<213> ORGANISM: Desulfovibrio vulgaris
<220> FEATURE:
<223> OTHER INFORMATION: Snbsr2 oligonucleotide, where H is A, C or T; K
      is G or T; Y is C or T; N is A,C, G or T

<400> SEQUENCE: 20
gacggttacg ghcckgtygg ygcntggttc ct                                   32

<210> SEQ ID NO 21
<211> LENGTH: 23
<212> TYPE: DNA
<213> ORGANISM: Desulfovibrio vulgaris
<220> FEATURE:
<223> OTHER INFORMATION: Snbsr3 oligonucleotide, where H is A,C or T; K
      is G or T; Y is C or T; N is A, C, G or T

<400> SEQUENCE: 21
gghcckgtyg gygcntggtt cct                                             23

<210> SEQ ID NO 22
<211> LENGTH: 23
<212> TYPE: DNA
<213> ORGANISM: Desulfovibrio vulgaris
<220> FEATURE:
<223> OTHER INFORMATION: Snbsr4 oligonucleotide, where K is G orT; S is
      C or G; R is A or G; B is G, C or T

<400> SEQUENCE: 22
tggttcctkc tsttcaargc baa                                             23

<210> SEQ ID NO 23
<211> LENGTH: 24
<212> TYPE: DNA
<213> ORGANISM: Desulfovibrio vulgaris
<220> FEATURE:
<223> OTHER INFORMATION: Snbsr5 oligonucleotide, where S is C or G; R is
      A or G; B is G, C or T;Y is C or T
```

```
<400> SEQUENCE: 23
ctsttcaarg cbaargcyac caac                                          24

<210> SEQ ID NO 24
<211> LENGTH: 26
<212> TYPE: DNA
<213> ORGANISM: Desulfovibrio vulgaris
<220> FEATURE:
<223> OTHER INFORMATION: Snbsr6 oligonucleotide, where V is A,C or G; S
      is C or G; R is A or G; Y is C or T

<400> SEQUENCE: 24
aaccgcgcva tgctsaarcc ytacga                                        26

<210> SEQ ID NO 25
<211> LENGTH: 26
<212> TYPE: DNA
<213> ORGANISM: Desulfovibrio vulgaris
<220> FEATURE:
<223> OTHER INFORMATION: Snbsr7 oligonucleotide, where  R is A or G;  W
      is A or T; H is A, C or T; M is A or C

<400> SEQUENCE: 25
tacgargawc gcgghtacgc maaggg                                        26
```

METHOD OF DETECTING SULPHATE-REDUCING BACTERIA

BACKGROUND OF THE INVENTION

1. Field of the Invention

The present invention relates to a method of detecting and enumerating sulphate-reducing bacteria.

2. Description of Related Art

Sulphate-reducing bacteria (SRB) use sulphate as electron acceptor under anaerobic conditions, via the anaerobic respiration of sulphates (energy reduction), to produce sulphides while recovering, during this reduction, the energy necessary for their growth. This metabolic characteristic constitutes a common characteristic of these organisms, regardless of their phylogenetic position (Legall & Fauques, 1988).

These bacteria are recognized to be the principal microorganisms responsible for the biological formation of hydrogen sulphide ($H_2S$). This $H_2S$ of biological origin in particular, and the metabolism of sulphate-reducing bacteria in general, cause many problems for industrialists such as the biological corrosion of steel, on the one hand, and the potential risk for staff, on the other (Postgate, 1979). In the petroleum industry, in addition to the abovementioned pernicious effects, the sulphate-reducing bacteria are also involved in impairing the quality of crude oil (Cord-Ruwich et al., 1987). The detection of these sulphurogenic bacteria therefore constitutes a major challenge for combating the production of $H_2S$ in a large number of industrial activities (Tatnall et al., 1988).

Microbial culture techniques applied to the detection and to the enumeration of these microorganisms have been developed (API, 1982; Magot et al., 1988; Scott & Davies, 1992). These methods require an incubation time of 10 to 21 days and are therefore poorly suited to the monitoring of contaminations of fluids in real time. Alternative methods allowing rapid measurement of the level of contamination have also been developed, such as for example the "Rapid Check™" from Conocco, based on the immunodetection of APS reductase (Horacek & Gawell, 1988, EP 272,916), or the "Hydrogenase test™" (Caproco), which detects the activity of hydrogenases, enzymes which are present in the SRBs but are not specific to these organisms (Scott & Davies, 1992). However, none of these methods is sufficiently sensitive or specific.

SUMMARY OF THE INVENTION

The authors of the present invention have developed a method of detecting and enumerating sulphate-reducing bacteria which combines these two advantages: sensitivity and specificity and which combines, in addition, speed with reliability. They therefore directed their attention to the sulphate energy reduction pathway and more specifically to that of APS reductase.

APS reductase (or Adenylylsulphate reductase) which allows the reduction of adenosine phosphosulphate (APS) (product of the activation of sulphate by ATP sulphurylase), is a cytoplasmic enzyme containing two subunits ($\alpha$ and $\beta$) known to be involved only in the anaerobic respiration of sulphate (Legall & Fauques, 1988). This enzyme is not therefore present in non-sulphate-reducing organisms since it is not involved in the assimilatory reduction which allows the incorporation of sulphur into various molecules necessary for life, such as amino acids and vitamins.

On the basis of two sequences of the gene encoding this enzyme deposited in data banks, one derived from an organism in the domain of Bacteria (*Desulfovibrio vulgaris*, em_ba: 269372) and the other from the sector of Archaea (*Archaeoglobus fulgidus:* em_ba: X63434), the authors of the present invention were able to amplify and sequence various genes encoding APS reductase. Surprisingly, they observed that this gene is remarkably well conserved whereas the phylogenetic diversity of the organisms studied could not a priori suggest it. This result opened the perspective for using this gene as a target for the specific detection of sulphate-reducing bacteria, especially in the domain of Bacteria.

The subject of the present invention is therefore the use of at least one nucleotide sequence which hybridizes specifically with a fragment of the APS reductase gene or a fragment of the mRNA transcribed from the APS reductase gene to detect the presence of sulphate-reducing bacteria in a sample.

DETAILED DESCRIPTION OF THE PREFERRED EMBODIMENT

The subject of the present invention is more particularly a method for the specific, qualitative or quantitative detection of sulphate-reducing bacteria in a sample which is likely to contain them, the said method comprising the extraction of the DNA or of the RNA from the said sample and the detection of at least one fragment of the APS reductase gene or one fragment of the mRNA transcribed from the APS reductase gene, an indicator of the presence of sulphate-reducing bacteria in the said sample.

The extraction of the DNA or of the RNA from the said sample may be carried out by standard techniques which are well known to persons skilled in the art.

More particularly, the detection of at least one fragment of the APS reductase gene comprises the specific gene amplification of at least one fragment of the gene for the $\alpha$ subunit of APS reductase. Advantageously, the gene amplification products may, in addition, be subjected to hybridization with a probe which is specific for the said fragment of the gene for the $\alpha$ subunit of APS reductase, the said probe being labelled in a detectable manner.

According to another embodiment, the detection of at least one fragment of the APS reductase gene comprises the hybridization of the extracted DNA with a probe which is specific for the said fragment of the gene for the $\alpha$ subunit of APS reductase, the said probe being labelled in a detectable manner.

According to another embodiment, the method of the invention comprises the extraction of the RNA from a sample which is likely to contain sulphate-reducing bacteria and the detection of at least one fragment of the mRNA which is transcribed from the APS reductase gene.

In this case, the detection may be carried out by direct hybridization of a specific nucleotide probe labelled in a detectable manner with the extracted mRNA, and/or by specific amplification of the mRNA encoding APS reductase, in particular by RT-PCR (reverse transcription followed by a polymerase chain reaction).

The subject of the present invention is also an oligonucleotide having a nucleotide sequence which is essentially identical to a sequence chosen from the sequences SEQ ID No. 1 to 25. Such an oligonucleotide is in particular useful as a primer for amplifying a fragment of the gene for the $\alpha$ subunit of APS reductase, or as a probe which hybridizes with a fragment of the gene for the $\alpha$ subunit of APS reductase or the product of amplification thereof.

Preferably, it is possible to use as a primer an oligonucleotide having a sequence which is essentially identical to one of the sequences SEQ ID No. 11 to 18, and as a probe an oligonucleotide having a sequence which is essentially identical to one of the sequences SEQ ID No. 19 to 25.

"Essentially identical" is understood to mean that the sequence of the oligonucleotide is identical to one of the sequences SEQ ID No. 1 to 25 or that it differs from one of these sequences without affecting the capacity of these sequences to hybridize with the gene for the α subunit of APS reductase. A sequence which is "essentially identical" to one of the sequences SEQ ID No. 1 to 25 may in particular differ therefrom by a substitution of one or more bases or by deletion of one or more bases located at the ends of the oligonucleotide, or alternatively by addition of one or more bases at the ends of the oligonucleotide. Preferably, such an oligonucleotide has a minimum size of 10 nucleotides, preferably of at least 14 nucleotides.

According to a preferred embodiment of the invention, the method of detecting sulphate-reducing bacteria in a sample which is likely to contain them according to the invention advantageously comprises the steps consisting in:

extracting the DNA from the said sample;

bringing the DNA extracted in step i) into contact with at least one primer consisting of an oligonucleotide having a nucleotide sequence which is essentially identical to a sequence chosen from the sequences SEQ ID No. 1 to 25, preferably No. 1 to 18, under conditions allowing the specific amplification of a fragment of the gene for the α subunit of APS reductase which may be present in the DNA extract;

bringing the product of amplification into contact with a probe consisting of an oligonucleotide having a nucleotide sequence which is essentially identical to a sequence chosen from the sequences SEQ ID No. 1 to 25, preferably No. 19 to 25, the said probe being labelled in a detectable manner, under conditions allowing the specific hybridization of the said product of amplification and the said probe;

detecting the hybridization complex formed between the product of amplification and the said probe, an indicator of the presence of sulphate-reducing bacteria in the sample.

"Conditions allowing the specific amplification" is understood to mean conditions of temperature, of reaction time and optionally the presence of additional agents which are necessary for the fragment of the gene for the α subunit of APS reductase, to which the primers as defined above have hybridized, to be copied identically.

Preferably, the amplification method used is a polymerase chain reaction (PCR) which is well known to persons skilled in the art (Sambrook et al., 1989), which uses a pair of primers as defined above.

"Conditions allowing the specific hybridization" is understood to mean high stringency conditions which prevent the hybridization of the oligonucleotide with sequences other than the gene for the α subunit of APS reductase.

The parameters defining the stringency conditions depend on the temperature at which 50% of the paired strands separate (Tm).

For the sequences comprising more than 30 bases, Tm is defined by the relationship: Tm=81.5+41(%G+C)+16.6 Log (concentration of cations)−0.63(%formamide)—(600/number of bases) (Sambrook et al., Molecular Cloning, A laboratory manual, Cold Spring Harbor laboratory Press, 1989, pages 9.54–9.62).

For the sequences of less than 30 bases in length, Tm is defined by the relationship:

$$Tm=4(G+C)+2(A+T).$$

Under appropriate stringency conditions, at which the aspecific sequences do not hybridize, the hybridization temperature is approximately 5 to 30° C., preferably 5 to 10° C. below Tm, and the hybridization buffers used are preferably solutions with a high ionic strength such as a 6×SSC solution, for example.

The oligonucleotide probes used in the method of the invention are labelled in a detectable manner. For that, several techniques are accessible to persons skilled in the art, such as for example fluorescent, radioactive, chemiluminescent or enzymatic labelling.

An internal amplification control may be advantageously used in order to avoid an ambiguous interpretation of negative results of the amplification method. Indeed, for example, an absence of amplification by PCR may be due to problems of inhibition of the reaction or to the absence of a target.

The authors of the present invention propose using, as an internal control, a plasmid including oligonucleotide sequences which allow the amplification of a fragment of the APS reductase gene, the said oligonucleotide sequences flanking a sequence differing from the said fragment of the APS reductase gene by its size and/or its sequence. The said oligonucleotide sequences which are specific for a fragment of the APS reductase gene may be chosen in particular from the sequences SEQ ID No. 1 to 25, preferably the sequences No. 11 to 18. An example of such a plasmid is represented in FIG. 4.

Added in a limiting concentration to the PCR reaction mixture, this plasmid allows the amplification of a DNA fragment of 289 bp (base pairs) when no specific target is present in the sample. Thus, in the example selected, the presence of a fragment of 289 bp, without a fragment of 205 bp, indicates the functioning of the reaction and the absence of a specific target, that is to say of sulphate-reducing bacteria from the sample studied.

The following examples and figures illustrate the invention without limiting the scope thereof.

EXAMPLES

Introduction

The experimental approach which resulted in the development of the method of the invention consists in:
1. The exploitation of the sequences of two genes for the α subunit of APS reductase which are available in data banks to construct various sets of amplification primers allowing the detection of new genes encoding this same enzyme and their sequencing.
2. The alignment of 7 sequences (2 derived from data banks and 5 obtained according to the approach detailed in point 1), making it possible to define conserved regions and to identify oligonucleotide sequences specific for this gene.
3. The evaluation of the specificity and of the sensitivity of the various sets of primers defined in point 2 on 10 strains of sulphate-reducing bacteria and 3 non-sulphate-reducing bacteria. A preferred pair of primers, leading to the amplification of a fragment of 205 bp, was validated on 36 other strains. The size of the PCR product derived from the pair of primers αsp01-αsp11 is 205 bp in the examples presented. However, it is not possible to exclude that this size varies according to the strains considered.
4. The control of the specificity of this pair of primers by sequencing 5 amplified fragments of 205 bp derived from new SRBs (with respect to point 2). The 11 SRB sequences of the Bacteria domain were aligned, which makes it possible to define nucleic probes, in the conserved regions of the fragment of 205 bp, which are capable of allowing the amplification or the specific detection of all or part of the gene.
5. The evaluation of the specificity and of the sensitivity of these oligonucleotides by membrane hybridization (Southern blotting).
6. The testing on microplates of a "sandwich" type nonradioactive hybridization protocol allowing specific visualization of the product of amplification of a fragment of this gene.
7. The definition of a complete protocol allowing the detection from field samples.
8. The correlation of the results obtained by this method with those obtained by the "Kits Labège BSR™" method from field samples.

The names of bacterial species mentioned in inverted commas refer to species described in the thesis by C. Tardy-Jacquenod (1996). These species were not validated by the international committees on nomenclature because they have not yet been the subject of a publication.

Example 1

Test for sequences encoding APS reductase in *Desulfovibrio* "tubi", *Desulfotomaculum nigrificans*, *Desulfomicrobium baculatum* and *Thermodesulfobacterium mobile*. Definition of specific and conserved primers.
a) Introduction Based on two APS reductase sequences deposited in international data banks (*Achaeoglobus fulgidus*: EMBL: X63435; *Desulfovibrio vulgaris*: EMBL No. Z69372), the authors of the present invention were able to define several pairs of primers capable of allowing the amplification of fragments of APS reductase. These amplified fragments were able to be sequenced, allowing comparison after alignment of the various sequences. Thus, the authors of the present invention were able to construct the various primers for the amplification which were specific for sulphate-reducing bacteria.
b) Materials and methods Sequences deposited in data banks. Two sequences encoding APS reductase are deposited in international data banks (GenBank and EMBL).

*Achaeoglobus fulgidus*: EMBL No. X63435
*Desulfovibrio vulgaris*: EMBL No. Z69372

Strains used.
SRL 7861 *Acheoglobus fulgidus*
SRL 4208 Non-identified fermentative anaerobic bacterium
SRL 3491 *Desulfomicrobium baculatum*
SRL 3096 *Desulfomicrobium baculatum*
SRL 583 *Desulfomicrobium nigrificans*
SRL 4225 *Desulfovibrio "bastinii"*
SRL 2840 *Desulfovibrio gabonensis*
SRL 3851 Desulfovibrio sp.
SRL 6143 *Desulfovibrio "tubi"*
SRL 4207 *Dethiosulfovibrio peptidovorans*
SRL 2668 *Thermodesulfobacterium mobile*
SRL 2801 *Thermodesulfobacterium mobile*
SRL 3138 *Thermatoga maritima*

DNA extractions.

The extractions of the DNAs from pure strains was carried out using the kit QIAamp Tissue Kit (QIAGEN, Hilden, Germany) according to the protocol given by the manufacturer.

PCR reactions.

The primers used for this study are given in Table 1.

TABLE 1

Primers constructed for the amplification of the APS reductase gene

| SEQ ID No. | Name of the primer | Oligonucleotide sequence | Position D. vulgaris | Orientation |
|---|---|---|---|---|
| 1 | APS01 | 5'-CGGCGCCGTTGCCCAGGG-3' | 957–974 | Sense |
| 2 | APS02 | 5'-TCTGTTCGAAGAGTGGGG-3' | 1110–1127 | Sense |
| 3 | APS03 | 5'-TTCAAGGACGGTTACGGC-3' | 1603–1620 | Sense |
| 4 | APS04 | 5'-CTTCAAGGACGGTTACGG-3' | 1602–1619 | Sense |
| 5 | APS05 | 5'-TCNGCCATHAAYACNTAC-3' | 979–996 | Sense |
| 6 | APS06 | 5'-GCAGATCATGATCAACGG-3' | 1239–1256 | Sense |
| 7 | APS11 | 5'-GGGCCGTAACCGTCCTTG-3' | 1605–1624 | Antisense |
| 8 | APS12 | 5'-TCACGAAGCACTTCCACT-3' | 2260–2671 | Antisense |
| 9 | APS13 | 5'-GCACATGTCGAGGAAGTC-3' | 1897–1914 | Antisense |
| 10 | APS14 | 5'-ACCGGAGGAGAACTTGTG-3' | 2161–2178 | Antisense | where
N: A, C, G or T
H: A, C or T
Y: C or T

The components of the gene amplification reactions (PCR) are given in Table 2.

TABLE 2

Components of the gene amplification reactions

| Reagents | Volumes | Final concentrations |
|---|---|---|
| Sense primer (20 μM) | 1.25 μl | 0.5 μM |
| Antisense primer (20 μM) | 1.25 μl | 0.5 μM |
| dNTP (10 mM each)[1] | 1 μl | 200 μM |
| PCR buffer 10X[1] | 5 μl | $MgCl_2$ = 1.5 mM |
| DNA | x μl | 2 ng/μl (that is 100 ng) |
| Taq DNA pol[1] | 0.4 μl | 2 U |
| H₂O | qs 50 μl | |

[1]Boehringer Mannheim SA (Meylan, France)

PCR programme:

| 1 cycle: | 3 min 95° C. |
| 5 cycles: | 1 min 94° C. |
| | 30 s X° C. |
| | T s 72° C. |
| 35 cycles: | 30 s 94° C. |
| | 30 s X° C. |
| | T s 72° C. |
| 1 cycle: | 5 min 72° C. |
| | hold 4° C. | where
T depends on the expected size of the amplified fragment: 1 min/kb

X is the hybridization temperature which depends on the pair of primers considered For a given primer $$X°C=Tm-4=4x(C+G)+2x(A+T)-4$$

For the analysis on a 1 or 2% agarose gel, 4 μl of PCR product were deposited, 1 μl Blue (Sambrook et al., 1989).

Sequencing of the amplified nucleic acids. The sequencing of the amplified nucleic acids was carried out directly on the crude PCR products.

Computer processing of the sequences: the Wisconsin Package programmes, version 9.1-unix, Genetics Computer Group (GCG), Madison, Wis., were used.

c) Results

Figure 1:
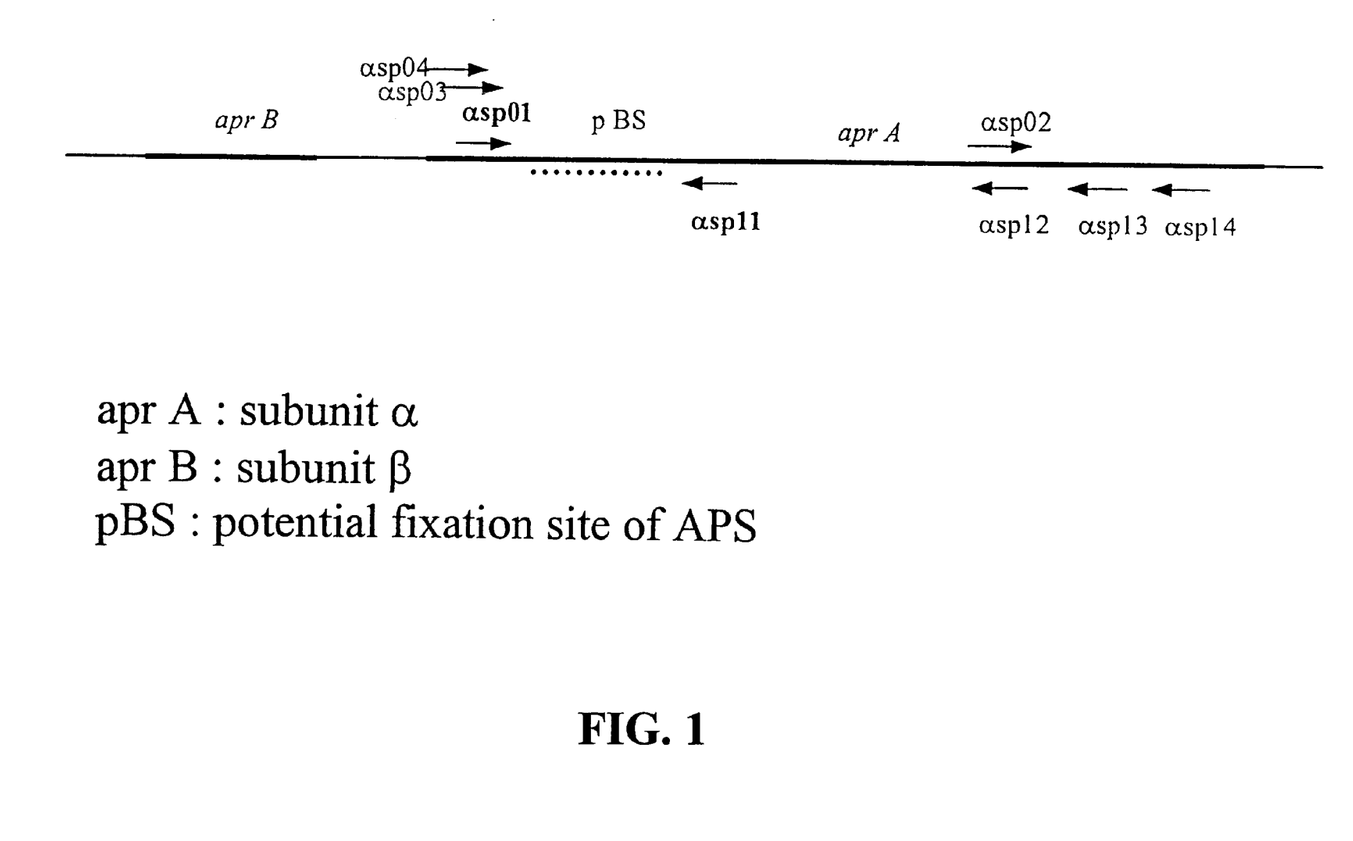
FIG. 1 represents the position of the various primers described in the examples of the α subunit of APS reductase.

The sequences of the *Desulfovibrio vulyaris* and *Archaeoglobus fulgidus* APS reductase genes available in the data banks were aligned. In the regions of homology detected, 10 oligonucleotide sequences capable of allowing the amplification of fragments of the a subunit of APS reductase were defined (cf. Table I). A fragment of 1580 bp of the *Desulfovibrio tubi* and *Desulfomicrobium baculatum* APS reductase gene was able to be amplified using the primers APS02 and APS12. In *Desulfotomacumul nigrificans* and the two strains of *Thermodesultobacterium mobile* (SRL2668 and SRL2801), this same fragment was amplified, in two stages, with the aid of the pairs of primers APS04–APS12 and APS02–APS13. The nucleotide sequence of the amplified fragments was determined. The alignment of these sequences shows that this gene is surprisingly well conserved in the sulphate reducing bacteria although the microorganisms studied are phylogenetically distant. This result suggests the potential use of this gene in the context of the detection of SRBs with the aid of molecular diagnostic methods. The authors of the present invention therefore, in order to validate this hypothesis, undertook the construction of new primers in some regions of the gene for the a subunit of APS reductase. These primers, which are located in FIG. 1, are presented in Table 3.

TABLE 3

Primers specific for the α subunit of APS reductase

| SEQ ID No. | Name of the primer | Oligonucleotide sequence | Position D. vulgaris | Orientation |
|---|---|---|---|---|
| 11 | αsp01 | 5'-GATGGAAAACCGCTTCG-3' | 1575–1591 | Sense |
| 12 | αsp02 | 5'-AAGTTCTCCTCCGGTTC-3' | 2164–2180 | Sense |
| 13 | αsp03 | 5'-ACCATGATGGAAAACCG-3' | 1570–1586 | Sense |
| 14 | αsp04 | 5'-TGACCATGATGGAAAAC-3' | 1568–1584 | Sense |
| 15 | αsp11 | 5'-CGAAGCATCATGTGGTT-3' | 1765–1781 | Antisense |
| 16 | αsp12 | 5'-CCGGAGGAGAACTTGTG-3' | 2161–2177 | Antisense |
| 17 | αsp13 | 5'-AGGCGCATCATGAAGTT-3' | 2371–2387 | Antisense |
| 18 | αsp14 | 5'-ATGTGCTGCATGTGCAG-3' | 2572–2588 | Antisense |

The various sets of primers thus constructed were tested on various genomic DNAs of sulphate-reducing (SRL 2668, 2801, 2840, 3096, 3491, 3851, 4225, 6143 and 7861) and non-sulphate-reducing (SRL 3138, 4207, and 4208) bacteria. All the sets of primers tested, with the exception of the αsp02–αsp14 set which does not allow amplification of the APS reductase of *Thermodesulfobacterium mobile* under the test conditions, allow a specific amplification of this gene in the SRBs.

The set of primers αsp01–αsp11, which leads to the amplification of a fragment of 205 base pairs (bp), was selected for a control screening on a large number of strains for the following reasons:

very good amplification yield, very little aspecificity, and primers delimiting the visibly well conserved 20 potential binding site of APS (Speich et al., 1994), which ought to facilitate the construction of other oligonucleotides allowing the specific detection of the amplification products or of the gene itself.

Example 2

Validation of the reference strains for the specificity of the primers αsp01–αsp11. Test for nucleic probes capable of allowing the visualization of the amplification products and definition of the detection threshold under field conditions.

a) Introduction.

The authors of the present invention then showed that the pair of primers selected makes it possible specifically to amplify an oligonucleotide sequence of 205 bp present only in the sulphate reducing bacteria. In addition, based on new nucleic sequences of the fragment of 205 bp, it was possible to define a set of probes which make it possible to visualize, for example, the specific amplification of the SRBs by hybridization. The results of a study aimed at evaluating the sensitivity threshold of the proposed method from a standardized suspension of *Desulfovibrio* "tubi" (SRL 6143).

b) Materials and methods

1)—Strains used. In addition to the strains cited in Example 1, the strains specifically used in this section are stated in Table 4, which is presented in section c) of this example.

2)—DNA extractions. Two nucleic acid extraction methods were used, one for the preparation of the DNAs of pure strains, the other for the preparation of nucleic acids from field samples. The latter method of extraction is that recommended for the kit itself and is used for the study presented in Example 3.

The extraction of the DNAs from pure strains is carried out using the kit: QIAamp Tissue Kit (QIAGEN, Hilden, Germany) according to the supplier's protocol.

The extraction of the nucleic acids for the detection of the SRBs in samples is carried out as follows: after centrifugation of 1 ml of sample for 30 min at 15,000 rpm, the supernatant is removed. 200 μl of InstaGene™ template (Bio-rad laboratories, Hercules, Calif.) (previously homogenized) are added to the pellet, the mixture is vortexed and incubated for 30 min at 56° C. The mixture is vortexed and placed for 8 min at 100° C. The sample is then centrifuged for 2 min at 12,000 rpm, it being possible for 20 μl of supernatant to be used directly in the PCR reactions. The remainder of the supernatant will be frozen if necessary.

3)—PCR reactions.

The composition of the reaction medium is presented in Table 2.

PCR programme

| 1 cycle: | 3 min 95° C. |
| 5 cycles: | 1 min 94° C. |

|         |                |
|---------|----------------|
|         | 30 s 54° C.    |
|         | 10 s 72° C.    |
| 35 cycles: | 30 s 94° C. |
|         | 30 s 54° C.    |
|         | 10 s 72° C.    |
| 1 cycle: | 5 min 72° C.  |
|         | hold 4° C.     |

For the analysis of the amplification products on 2% agarose gel, 5 µl are deposited, 1 µl of Blue (Sambrook et al., 1989) for the pure strains.

4) Southern blotting

Deposition on 2% agarose gel of 8 µl of amplification product+2 µl Blue (Sambrook et al., 1989) per well Migration at 100V for 2 h 0 min EtBr staining, destaining, photography Treatment of the gel:

Depurination: 0.25 M HCl: 10 min after destaining blue>yellow (rinsing $H_2O$)

Denaturation: 0.5 M NaOH, 1.5 M, NaCl: 15 min after restaining yellow>blue (rinsing $H_2O$)

Neutralizing: 0.5 M Tris pH 8, 1.5 M NaCl: 2×10 min

Transfer onto Hybond N+ film for 4 h 30 min at room temperature by capillarity in a 20×SSC solution Post-transfer treatments:

labelling of the wells attaching of the DNA to the membrane for 15 min on a Whatman sheet of paper impregnated with 0.4 N NaOH rinsing 1 min with 5×SSC Prehybridization 1 h at 42° C. in:

5×SSC (Sambrook et al., 1989)

5× Denhardt's (Sambrook et al., 1989)

0.5% SDS

100 µg/ml of fish sperm DNA (sonicated and denatured) (DNA, MB grade, from fish sperm, Boehringer Mannheim S.A., Meylan, France)

Labelling of the probe with terminal transferase:

Enzymatic reaction:

2 µl of probe at 50 ng/µl

1 µl of TdT mixture

5 µl of [$^{32}$P]dCTP, that is 50 µCi

1 µl of terminal transferase (Pharmacia Biotech)

1 µl of DTT at 1 mM

Incubation 15 min at 37° C.

Addition of 10 µl of $H_2O$ and 5 µl of 2% SDS-5 mM EDTA

Elimination of the oligonucleotides not incorporated by P6 column (Bio-rad laboratories, Hercules, Calif.)

Hybridization 16 h at 42° C. in prehybridization buffer+ labelled probe activity=$10^6$ cpm/ml of buffer Rinsing: 2×SSC 0.1% SDS at room temperature Washing: 2×SSC 0.1% SDS at room temperature 15 min 2×SSC 0.1% SDS at 50° C. 30 min 1×SSC 0.1% SDS at 50° C. 30 min 0.1×SSC 0.1% SDS at 50° C. 30 min Exposure at −80° C. for 5 h 0 min on X-OMAT™ (Kodak, Rochester, N.Y.).

5)—Test of the probes in microplates according to the sandwich hybridization method. Microplates were sensitized in a passive manner with the probe Snbsr 2, used as capture probe which is internal to the amplified product (cf. Table 5). After incubating for 16 to 18 hours, the wells are washed and the plates stored at 4° C. The visualization of the amplified products is made possible by a peroxidase-labelled internal revealing probe (the probes Snbsr 6 and Snbsr 7 were tested independently during this study). The protocol recommended in the Probélia™ kits (SANOFI Diagnostics Pasteur) was used for carrying out the hybridization and detection steps.

6)—Sequencing of the amplified nucleic acids. The sequencing of the amplified nucleic acids was carried out directly on the crude PCR products.

7)—Computer processing of the sequences. The Wisconsin Package programmes, version 9.1-unix, Genetics Computer Group (GCG), Madison, Wis., were used.

c) Results

The specificity of the set of primers αsp01–αsp11 was evaluated on 37 genomic DNAs of pure strains extracted from sulphate-reducing and non-sulphate-reducing bacteria. The results obtained, which are given in Table 4, show that the pair of primers defined indeed allows specific amplification of a fragment of the APS reductase gene of sulphate-reducing bacteria.

TABLE 4

Evaluation of the specificity of the pair of primers αsp01–αsp11

| Strains | Name | Amplification of the specific fragment of ASP reductase |
|---------|------|---------------------------------------------------------|
| SRB     |      |                                                         |
| SRL 4594 | *Desulfovibrio desulfuricans* | + |
| SRL 6146 | *Desulfovibrio "gracilis"* | + |
| SRL 422 | *Desulfovibrio desulfuricans* | + |
| SRL 4596 | *Desulfovibrio sp.* | + |
| SRL 3707 | *Desulfovibrio desulfuricans* | + |
| SRL 3137 | *Desulfovibrio sp.* | + |
| SRL 2811 | *Desulfovibrio "caledoniensis"* | + |
| SRL 2976 | *Desulfovibrio desulfuricans* | + |
| SRL 1234 | NI* SRB | + |
| SRL 3688 | *Desulfovibrio desulfuricans* | + |
| SRL 3920 | *Desulfovibrio desulfuricans* | + |
| SRL 3663 | *Desulfovibrio desulfuricans* | + |
| SRL 3698 | *Desulfovibrio desulfuricans* | + |
| SRL 2582 | *Desulfovibrio longus* | + |
| SRL 2683 | *Desulfovibrio desulfuricans* | + |
| SRL 2810 | *Desulfovibrio desulfuricans* | + |
| SRL 3664 | *Desulfovibrio desulfuricans* | + |
| SRL 3920 | *Desulfovibrio desulfuricans* | + |
| SRL 3096 | *Desulfomicrobium baculatum* | + |
| SRL 3709 | *Desulfovibrio desulfuricans* | + |
| SRL 3697 | *Desulfovibrio desulfuricans* | + |
| SRL 3706 | *Desulfovibrio desulfuricans* | + |
| SRL 3101 | *Desulfovibrio lonreachii* | + |
| SRL 3664 | *Desulfovibrio desulfuricans* | + |
| SRL 3863 | *Desulfovibrio "gracilis"* | + |
| SRL 3699 | *Desulfovibrio desulfuricans* | + |
| SRL 3685 | *Desulfovibrio desulfuricans* | + |
| SRL 3708 | *Desulfovibrio desulfuricans* | + |
| SRL 2979 | *Desulfohalobium retbaense* | + |
| Non-SRB |      |                                                         |
| SRL 4227 | NI* fermentative | − |
| SRL 2471 | *Haloanaerobium acetoethylicus* | − |
| SRL 4226 | *Dethiosulfovibrio peptidovorans* | − |
| SRL 4234 | *Geotoga subterranea* | − |
| SRL 4224 | *Haloanaerobium congolense* | − |
| SRL 4205 | NI* fermentative | − |
| SRL 618 | *Clostridium glycolicum* | − |

*NI: non-identified

Definition of the internal amplification control.

Figure 2:
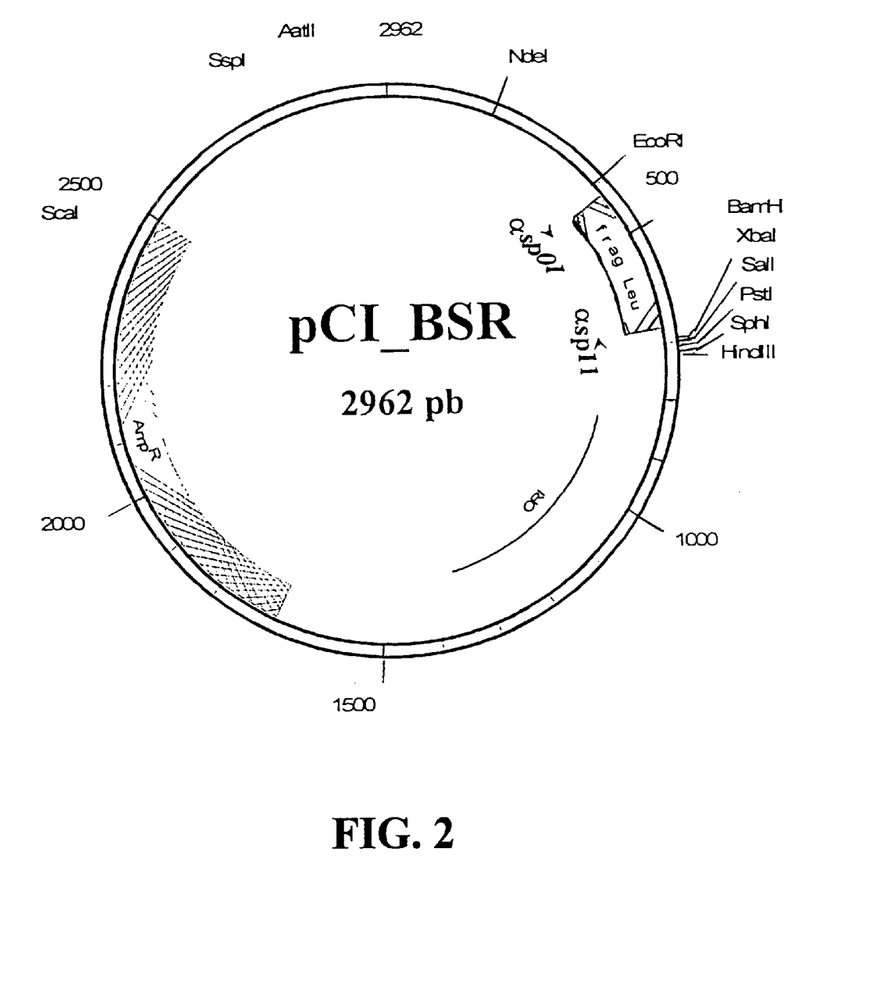
FIG. 2 represents the restriction map of the plasmid pCI BSR used as an internal control, obtained from a plasmid pUC19.
Figure 3:
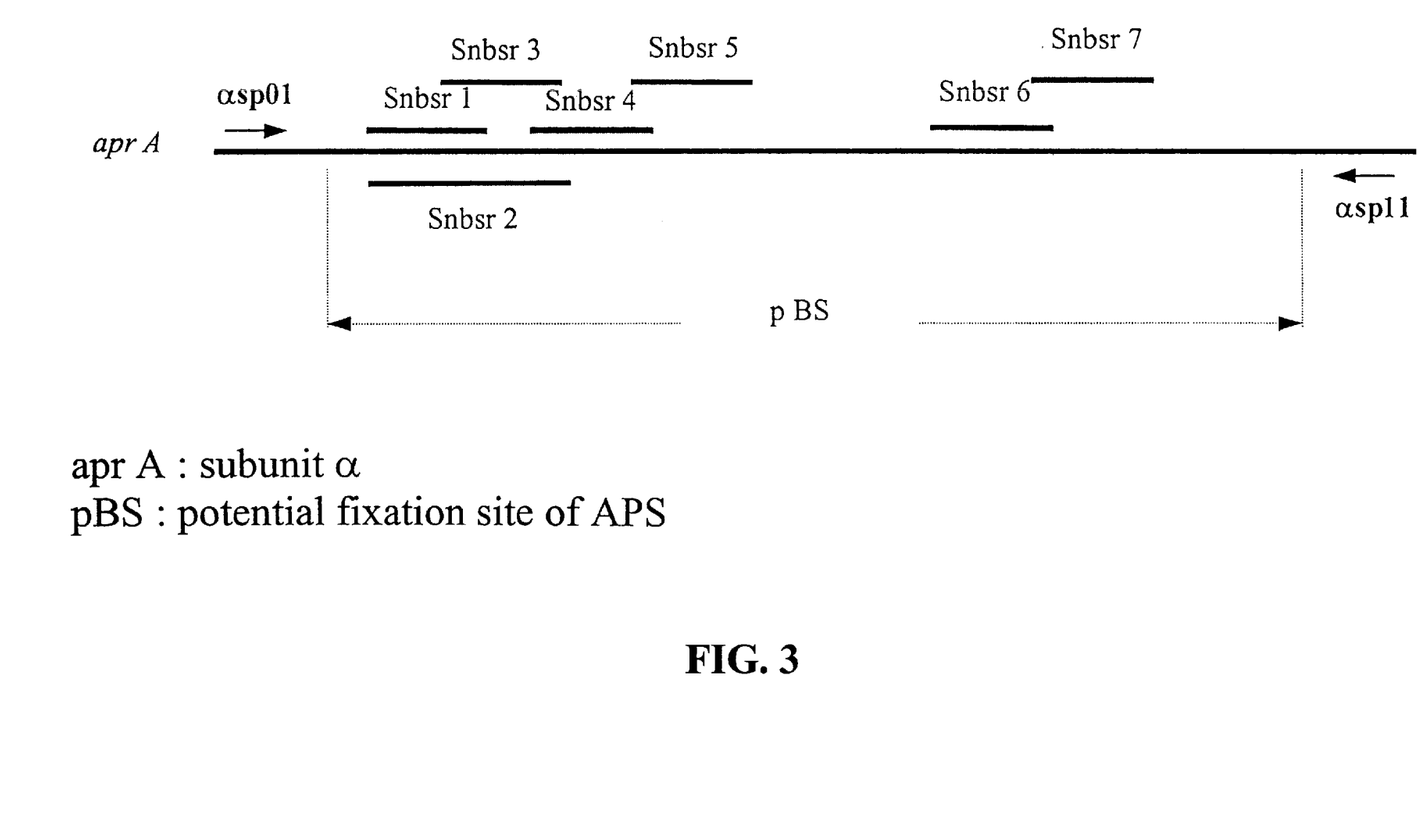
FIG. 3 represents the position of the various oligonucleotides which hybridize specifically between the primers asp01 and asp11 in APS reductase.

To avoid ambiguous interpretation of the negative results of the PCRs (an absence of amplification by PCR may be due to problems of inhibition of the reaction or to the absence of a target), a plasmid (FIG. 2) was constructed. Added in a limiting concentration to the PCR reaction mixture, this plasmid allows the amplification of a DNA fragment of 289 bp when no specific target is present in the sample. Thus, in the example selected, the presence of a fragment of 289 bp, without a fragment of 205 bp, indicates the functioning of the reaction and the absence of a specific target, that is to say of sulphate-reducing bacteria, from the sample studied. In addition, the sequence intercalated between the primers αsp01 and αsp11 in the internal control differs by its size but also by its sequence (Leu2 gene) thus making it possible not to confuse the amplification of the bium baculatum (SRL 3096), Desulfovibrio longreachii (SRL 3101), Desulfotribrio "gracilis" (SRL 6146), Desulfovibrio desulfuricans (SRL 3707) and Thermodesulfobacterium mobile (SRL 2668) were sequenced in order to verify the specificity of the amplifications. The alignment of all the available sequences shows that the remarkable conservation of the gene in this region makes it possible to define 7 new oligonucleotide sequences which can be potentially used for the detection of the gene, or of a fragment of this gene by hybridization or gene amplification (Tab. 5 and FIG. 3).

TABLE 5

Oligonucleotides hybridizing specifically in the fragment between primers αsp01 and αsp11 of the α subunit of APS reductase.

| SEQ ID No. | Name | Oligonucleotide sequence | Position D. vulgaris | Orientation |
|---|---|---|---|---|
| 19 | Snbsr1 | 5'-GACGGTTACGGHCCKGTYGGYGC-3' | 1609–1631 | Sense |
| 20 | Snbsr2 | 5'-GACGGTTACGGHCCKGTYGGYGCNTGGTTCCT-3' | 1609–1640 | Sense |
| 21 | Snbsr3 | 5'-GGHCCKGTYGGYGCNTGGTTCCT-3' | 1618–1640 | Sense |
| 22 | Snbsr4 | 5'-TGGTTCCTKCTSTTCAARGCBAA-3' | 1630–1655 | Sense |
| 23 | Snbsr5 | 5'-CTSTTCAARGCBAAPGCYACCAAC-3' | 1642–1665 | Sense |
| 24 | Snbsr6 | 5'-AACCGCGCVATGCTSAARCCYTACGA-3' | 1693–1718 | Sense |
| 25 | Snbsr7 | 5'-TACGARGAWCGCGGHTACGCMAAGGG-3' | 1714–1739 | Sense | where
N: A, C, G or T  H: A, C or T
B: G, C or T  V: A, C or G
Y: C or T  M: A or C
W: A or T  K: G or T
S: C or G  R: A or G internal control with the specific amplification of a fragment of the APS reductase gene whether the PCR analysis is performed on agarose gel or by hybridization. In the example selected, the fragment of 255 bp of the *Sacchazromycea cerevisiae* Leu2 gene was chosen, but any nucleotide sequence may be used provided that it has no homology with the fragment of 205 bp of the APS reductase gene.

It will be noted that this plasmid can only be used as internal control during the detection of sulphate-reducing bacteria with the set of primers αsp01–αsp11. Nevertheless, similar controls can be constructed on the same model in order to make it possible to validate the negative results indicating an absence of a target.

Evaluation of the sensitivity threshold

A cellular suspension of *Desulfovibrio "tubi"* at $10^8$ cells/ml was prepared. It was standardized by dilution in liquid medium by the 3-tube most-probable-number method in the optimum culture medium for the strain (Tardy-Jacquenod, 1996). The evaluation of the sensitivity threshold for the gene amplification was carried out by a 10-fold serial dilution of the cellular suspension and extraction of the nucleic acids according to the InstaGene™ method. By subjecting each nucleic acid extract thus obtained to the PCR test, the authors of the present invention were able to show that the detection of 10 bacteria/ml was possible with the set of primers developed in the presence of an internal control which makes it possible to validate the negative results. These experiments were visualized on agarose gel.

Probes for visualizing the specific amplifications.

Five amplification products obtained with the pair of primers αsp01–αsp11 from genomic DNA of *Desulfomicro-*

These oligonucleotides were tested as probes for the detection of the amplification product of 205 bp by membrane hybridization (Southern blotting). Amplification products obtained with the pair of primers αsp01–αsp11 from genomic DNA of pure strains of sulphate-reducing bacteria (SRL 4225, SRL 6143, SRL 3851, SRL 3492, SRL 2668, SRL 2801) or non-sulphate-reducing bacteria (SRL 4208, SRL 4207, SRL 4226, SRL 6459, SRL 5268, SRL 7311, SRL 3138, SRL 4224) were used in this study.

The results of the hybridization experiments with the probe Snbsr 3 are summarized in Table 6.

TABLE 6

Test of the probes for visualizing the amplification products on membranes (Southern blotting)

| Probe | Size | Specificity[1] | Sensitivity[2] | Remarks |
|---|---|---|---|---|
| Snbsr 1 | 23-mers | OK | OK | |
| Snbsr 2 | 32-mers | OK | OK | capture test |
| Snbsr 3 | 23-mers | OK | OK | |
| Snbsr 4 | 23-mers | OK | | |
| Snbsr 5 | 24-mers | OK | | |
| Snbsr 6 | 26-mers | OK | OK | visualization test |
| Snbsr 7 | 26-mers | OK | OK | visualization test |

[1]Capacity to hybridize only with the PCR products specific to the SRBs (αsp01–αsp11 fragment) in the α subunit of APS reductase.
[2]Allows hybridization with all the PCR products specific to the SRBs αsp01–αsp11 fragment) in the α subunit of APS reductase regardless of the strain of origin.

Example of use of the oligonucleotides defined in this work in a "sandwich" type non-radioactive hybridization system.

On the basis of the results obtained by membrane hybridization, a study designed to evaluate a system for detecting the amplification products in microplates, by a "sandwich" type non-radioactive hybridization technique, was undertaken.

The results presented in Tables 7a, 7b and 7c show that the use of the probes selected (Snbsr 2 with Snbsr 6 or Snbsr 7) is possible in terms of sensitivity and specificity for the detection of amplification products obtained with the pair of primers αsp01–αsp11. However, the pair Snbsr 2–Snbsr 6 will be preferred for its sensitivity (difference in values between the blanks and the positive samples).

TABLE 7a

Results of the hybridization tests in microplates with the probe Snbsr 2 used as capture probe and Snbsr 6 or Snbsr 7 labelled with peroxidase as revealing probe. Amplification experiment in the absence of internal control on pure strains

| | | | Snbsr 2 - Snbsr 6 | | Snbsr 2 - Snbsr 7 | |
|---|---|---|---|---|---|---|
| | SRL | αsp01-αsp11 amplif. of | $OD_{405\,nm}$ | Interpret. | $OD_{406\,nm}$ | Interpret. |
| Blanks | | without ampl. | 0.159 | / | 0.045 | / |
| | | without ampl. | 0.171 | / | 0.052 | / |
| | | $H_2O$ | 0.096 | / | 0.018 | / |
| | | $H_2O$ | 0.137 | / | 0.027 | / |
| SBR | 61 | Desulfovibrio "tubi⇆ | >3 | + | 0.353 | + |
| | 43 | Desulfovibrio "bastinii" | >3 | + | 2.223 | + |
| | 42 | Desulfomicrobium baculatum | 2.150 | + | 1.053 | + |
| | 25 | Desulfomicrobium baculatum | 0.562 | + | 0.211 | + |
| | 38 | Desulfotomaculum nigrifians | >3 | + | 1.773 | + |
| | 51 | Thermodesulfobacterium mobile | 0.963 | + | 0.586 | + |
| | 34 | Thermodesulfobacterium mobile | 1.570 | + | 0.422 | + |
| SRB | 3 | | | | | |
| | 26 | | | | | |
| | 68 | | | | | |
| | 28 | | | | | |
| | 01 | | | | | |
| Non-SRB | 64 | Thermotoga elfii | 0.117 | — | 0.025 | — |
| | 59 | NI* fermentative | 0.139 | — | 0.032 | — |
| | 42 | Dethiosulfovibrio peptidovorans | 0.094 | — | 0.019 | — |
| | 08 | Thermoanaerobacter brockii subsp. lactiethylicus | 0.098 | — | 0.017 | — |
| | 42 | Thermatoga maritima | 0.099 | — | 0.021 | — |
| | 07 | Haloanaerobium congolense | 0.106 | — | 0.014 | — |
| | 52 | Thiobacillus ferroxydans | 0.181 | — | 0.041 | — |
| | 68 | | | | | |
| | 31 | | | | | |
| | 38 | | | | | |
| | 42 | | | | | |
| | 24 | | | | | |
| | 78 | | | | | |
| | 64 | | | | | |

*NI non identified

TABLE 7b

Results of the hybridization tests in microplates with the probe Snbsr 2 used as capture probe and Snbsr 6 or Snbsr 7 labelled with peroxidase as revealing probe. Amplification experiment in the presence of internal control on pure strains

| | | | Snbsr 2 - Snbsr 6 | | Snbsr 2 - Snbsr 7 | |
|---|---|---|---|---|---|---|
| | SRL | αsp01-αsp11 amplif. of | $OD_{405\,nm}$ | Interpret. | $OD_{406\,nm}$ | Interpret. |
| Blanks | | without ampl. | 0.159 | / | 0.045 | / |
| | | without ampl. | 0.174 | / | 0.052 | / |

TABLE 7b-continued

Results of the hybridization tests in microplates with the probe Snbsr 2 used as capture probe and Snbsr 6 or Snbsr 7 labelled with peroxidase as revealing probe. Amplification experiment in the presence of internal control on pure strains

|  |  |  | Snbsr 2 - Snbsr 6 | | Snbsr 2 - Snbsr 7 | |
|---|---|---|---|---|---|---|
|  | SRL | αsp01–αsp11 amplif. of | $OD_{405\ nm}$ | Interpret. | $OD_{406\ nm}$ | Interpret. |
| SBR |  | $H_2O$ | 0.271 | / | 0.051 | / |
|  |  | $H_2O$ | 0.299 | / | 0.069 | / |
|  |  | Desulfovibrio "tubi≤" | >3 | + | 0.321 | + |
|  |  | Desulfovibrio "bastinii" | >3 | + | 2.138 | + |
|  |  | Desulfomicrobium baculatum | 2.28 | + | 1.160 | + |
|  |  | Desulfomicrobium baculatum | 0.667 | + | 0.214 | + |
|  |  | Desulfotomaculum nigrifians | >3 | + | 1.564 | + |
|  |  | Thermodesulfobacterium mobile | 0.17 | + | 0.715 | + |
|  |  | Thermodesulfobacterium mobile | 0.889 | + | 0.282 | + |
| Non-SRB |  | Thermotoga elfii | 0.246 | — | 0.056 | — |
|  |  | NI* fermentative | 0.096 | — | 0.037 | — |
|  |  | Dethiosulfovibrio peptidovorans | 0.088 | — | 0.021 | — |
|  |  | Thermoanaerobacter brockii subsp. laciethylicus | 0.106 | — | 0.020 | — |
|  |  | Thermatoga maritima | 0.221 | — | 0.025 | — |
|  |  | Haloanaerobium congolense Thiobacillus ferroxydans | 0.039 | — | 0.029 | — |
|  |  |  | 0.199 | — | 0.042 | — |

*NI non identified

TABLE 7c

Results of the hybridization tests in microplates with the probe Snbsr 2 used as capture probe and Snbsr 6 or Snbsr 7 labelled with peroxidase as revealing probe. Amplification experiment in the presence of internal control on field samples

|  |  | αsp01–αsp11 amplif. of | SRB/ml "Labège BSR ™ kits" | Snbsr 2–Snbsr 6 | | Snbsr 2–Snbsr 7 | |
|---|---|---|---|---|---|---|---|
| SRL |  |  |  | $OD_{405\ nm}$ | Inter-pret. | $OD_{405\ nm}$ | Inter-pret. |
| Blanks |  | without ampl. | / | 0.159 | / | 0.045 | / |
|  |  | without ampl. | / | 0.174 | / | 0.052 | / |
|  |  | $H_2O$ | / | 0.271 | / | 0.051 | / |
|  |  | $H_2O$ | / | 0.299 | / | 0.069 | / |
| Sample |  | CM 1 | $2.5\ 10^8$ | 2.475* | + | 0.663* | + |
|  |  | CM 2 | <0.3 | 0.088 | – | 0.014 | – |

*measured from a PCR amplification carried out at the $10^{-4}$ dilution of the sample

Example 3

Correlation of the results obtained by the gene amplification and conventional culture methods a) Introduction The object of this example is to compare the results of the enumeration of the SRBs in the samples by the gene amplification method (using the oligonucleotides defined in this work) and by the reference culture method. For the latter, the "Labège BSR™ Kits" (CFG, Orléans, France) were used, these kits constituting the most sensitive tests on the market.

b) Materials and methods

Samples:
Water from aquifers, edgewater and annular fluids from oil wells.

DNA extractions

The extraction of the nucleic acids for the detection of the SRBs from field samples (InstaGene™ method, Bio-rad laboratories, Hercules, Calif.) was carried out as follows: centrifuge 1 ml of sample for 30 min at 15,000 rpm and then remove the supernatant. Add 200 μl of InstaGene™ matrix (previously homogenized) to the pellet, vortex and incubate for 30 min at 56° C. Vortex and place for 8 min at 100° C. The sample is then centrifuged for 2 min at 12,000 rpm. In the PCR reactions, 20 μl of supernatant are used. The remainder of the supernatant is frozen if necessary.

PCR reactions for the detection of the SRBs

For the routine detection of the sulphate-reducing bacteria, an amplification system which makes it possible to limit the risks of contamination of the PCRs due to the extreme sensitivity of this mode of detection can be used. In this work, the "Core kit Plus™" (Boehringer Mannheim SA, Meylan, France) was used. The reaction conditions are given in Table 8.

TABLE 8

PCR reactions for the detection of the SRBs under field conditions

| Reagents | Volumes | Final concentrations |
|---|---|---|
| Primer asp01 (20 µM) | 1.25 µl | 0.5 µM |
| Primer asp11 (20 µM) | 1.25 µl | 0.5 µM |
| dNTP[1] | 1 µl | 200 µM |
| 10X[1] PCR buffer 25 mM MgCl$_2$ | 5 µl | |
| MgCl$_2$ (25 mM)[1] | 3 µl | 1.5 mM (+2.5 in) buffer) |
| Cl (Mini-prep at 10$^{-9}$) | 2 µl | ? |
| DNA prep | 20 µl | |
| UDG[1] | 1 µl | 1 U |
| Taq Dna pol[1] | 0.5 µl | 2.5 U |
| H$_2$O | qs 50 µl | |

[1]Boehringer Mannheim S.A. reagents (Meylan, France) PCR Core Kit Plus

Gel analysis: 16 µl of PCR products+4 µl Blue (Sambrook et al., 1989)

PCR enumeration

The enumeration of the SRBs is carried out by 10-fold serial dilution of the nucleic acid extracts, each dilution then being subjected to a PCR reaction. The interpretation of the result, in terms of number of SRB/ml, is given in Table 9 defined on the basis of the sensitivity threshold measured on a standardized cellular suspension of a pure strain (cf. Example 2).

TABLE 9

Principle of the enumeration of the SRBs by PCR.

| Reading of the specific amplification of the SRBs | Reading of the specific amplification of the control | Enumeration |
|---|---|---|
| Positive up to the dilution: | | |
| Not diluted | Not applicable | 10 to 10$^2$ SRB/ml |
| 10$^{-1}$ | Not applicable | 10$^2$ to 10$^3$ SRB/ml |
| 10$^{-2}$ | Not applicable | 10$^3$ to 10$^4$ SRB/ml |
| 10$^{-3}$ | Not applicable | 10$^4$ to 10$^5$ SRB/ml |
| 10$^{-4}$ | Not applicable | 10$^5$ to 10$^6$ SRB/ml |
| 10$^{-5}$ | Not applicable | 10$^6$ to 10$^7$ SRB/ml |
| 10$^{-6}$ | Not applicable | >10$^7$ SRB/ml |
| Negative | Positive | <10 SRB/ml |
| Negative | Positive from 10$^{-1(1)}$ | <100 SRB/ml |
| Negative | Negative[2] | Anomaly |

[1]In this case, the PCR reaction is only inhibited when the sample is not diluted.
[2]Absence of amplification due to an experimental anomaly Enumeration by culture: "Labège BSR™ Kits"

The enumerations are carried out according to the manufacturer's protocol (CFG, Orléans, France). The two methods proposed were used according to the samples:

Series of dilutions with 3 tubes (most-probable-number method—MPN) interpreted by the Mc Crady tables.

Single (1 tube) 10-fold series dilutions. The result obtained is then a "range".

c) Results

The results obtained on various field samples (obtained from water from aquifers, edgewater or annular fluids from oil wells) are summarized in Tables 10a and 10b.

TABLE 10a

Summary of the tests carried out using field sample

| Total number of analyses | Negative results by the 2 methods | Results <10 by culture and negative by PCR* | Results correlate see Tab. 1b |
|---|---|---|---|
| 35 | 13 | 6 | 16 |

*Less than the PCR detection threshold

The negative results were validated (specific amplification of the internal control)

TABLE 10b

Correlation between the microbiological and PCR enumerations

| | Results in SRB/ml | |
|---|---|---|
| Samples | Cultures[1] | PCR[2] |
| 1 | 2.5 10$^1$ | <10$^2$ |
| 2 | 2.5 10$^5$ | 10$^5$–10$^6$ |
| 3 | 9.5 10$^4$ | 10$^4$–10$^5$ |
| 4 | <0.3 | 10$^1$–10$^2$ |
| 5 | 0.09 | 10$^2$–10$^3$ |
| 6 | <0.3 | 10$^1$–10$^2$ |
| 7 | <0.3 | 10$^1$–10$^2$ |
| 8 | <0.3 | 10$^1$–10$^2$ |
| 9 | 2.5 10$^2$ | 10$^2$–10$^3$ |
| 10 | 10$^1$–10$^2$ | 10$^2$–10$^3$ |
| 11 | 10$^3$–10$^4$ | 10$^2$–10$^3$ |
| 12 | 10$^3$–10$^4$ | 10$^2$–10$^3$ |
| 13 | 10$^5$–10$^6$ | 10$^3$–10$^4$ |
| 14 | 9.5 10$^4$ | 10$^4$–10$^5$ |
| 15 | 9.5 10$^2$ | 10$^2$–10$^3$ |
| 16 | 10$^2$ | <10$^2$ |

[1]"Labège BSR ™ Kits": results obtained after 21 days of incubation.
[2]Results obtained in 4 hours.

Twenty six samples give a coherent result by the two methods (of which 20 in Table 10a and 6 in Table 10b).

The gene amplification method is more sensitive in 6 cases.

The culture method is found to be more sensitive for 4 samples.

It should be noted that when differences were observed, the enumerations obtained most often only differ by a factor of 10, never by more than a factor of 100, and that these differences are partly due to the fact that the interpretation is made on a range of values.

In addition to the value of the technique presented in terms of speed, the correlation studies presented above show that the PCR method applied to the enumeration of sulphate-reducing bacteria according to the method of use presented here leads to an estimation of the sulphate-reducing bacterial load which is quite comparable with that given by the "Labège BSR™ Kits". Moreover, these results confirm the detection threshold estimated on pure strains under field conditions, since the enumerations carried out by PCR assume that the sensitivity of detection is 10 SRB/ml (cf. sensitivity test, Example 2).

The method of the invention allows the detection and enumeration of sulphate-reducing bacteria from field samples. It also makes it possible to fulfil the criteria of sensitivity and speed but also of specificity and reliability inherent to the technique. In addition, this method is not subject to any artefact linked to the method itself: no problem of inhibition of the amplification reaction for a critical detection threshold of less than 100 SRB/ml (even when the sample collected is from an installation treated with biocides), no detection of dead bacteria.

BIBLIOGRAPHIC REFERENCES

API (1982) Recommended Practice for Biological Analysis of Subsurface Injection Waters American Petroleum Institute, Washington, D.C.

Cord-Ruwich R, Kleinitz W & Widdel F (1987) Sulphate-reducing bacteria and their activities in oil production. J. Petrol. Technol. 1: 97–106.

Horacek G. L. & Gawel L. J. (1988) New test kit for the rapid detection of SRB in the oil field. Proceedings of the 63rd American Society of Petroleum Engineers, Houston Oct. 2–5, 1988. SPE paper 18199. Society of Petroleum Engineers, Richardson, Tex.

LeGall J. & Fauque G. (1988) Dissimilatory reduction of sulfur compounds. In: A. J. Zehnder (ed.) Biology of anaerobic microorganisms, pp 587–639. John Wiley & Sons, New York.

Magot M., Mondell M. L., Ausseur J. & Seureau J. (1988). Detection of sulphate-reducing bacteria. In: C. C. Gaylarde and L. H. G. Morton "Biocorrosion; proceedings of a joint meeting between the Biodeterioration Society and the French Microbial Corrosion Group" pp 37–52. Biodeterioration Society, Kew, UK.

Postgate J. R. (1979). The sulphate-reducing bacteria. Cambridge University Press, London.

Sambrook J., Fritsch E. F. & Maniatis T. (1989) Molecular cloning—A laboratory manual. Second edition. Cold Spring Harbor Laboratory Press, Cold Spring Harbor, N.Y.

Scott P. J. B. & Davies M. (1992) Survey of field kits for sulfate-reducing bacteria. Materials Performance, May 1992, 64–68.

Speich N., Dahl C., Heisig P. Klein A., Lottspeich F., Stetter K. O. & Trüper H. G. (1994). Adenylylsulphate reductase from sulphate-reducing archaeon Archaeoglobus fulgidus: cloning and characterization of the genes and comparison of the enzyme with other iron sulphur flavoproteins. Microbiology 140: 1273–1284.

Tardy-Jacquenod C. (1996) Biodiversity, taxonomy and phylogeny of sulphate-reducing bacteria isolated from oil fields: examples of salty and hot deposits. Doctoral thesis. University of Bordeaux I.

Tatnall R. E., Stanton K. M. & Ebersole R. C. (1988) Testing for the presence of sulfate-reducing bacteria. Materials Performance, August 1988, 71–80.

Widdel, F. (1988) Microbiology and ecology of sulfate- and sulfur-reducing bacteria. In: Zehnder A. J. B. Biology of anaerobic microorganisms pp 469–585. John Wiley & Sons, New York.

What is claimed is:

1. A method for detection and enumeration of sulfate-reducing bacteria in a water sample, said method comprising:

extracting DNA or RNA from the water sample;

amplifying the DNA or the RNA in the presence of at least one primer selected from the group consisting of SEQ ID Nos: 11–18, said at least one primer being specific for amplification of at least a fragment of the α subunit of APS reductase gene;

hybridizing the amplification product with a probe which is specific for the fragment of the α subunit of APS reductase gene;

detecting a presence of hybridization and a degree of hybridization, wherein the presence of hybridization indicates the presence of the sulfate-reducing bacteria and the degree of hybridization enumerates the sulfate-reducing bacteria.

2. The method of claim 1, wherein the probe has a nucleotide sequence which specifically hybridizes under highly stringent conditions to the complement of at least one of SEQ ID Nos: 19 to 25.

3. The method of claim 1, wherein the probe is detectably labeled.

* * * * *